United States Patent [19]

Giglio et al.

[11] Patent Number: 4,755,052
[45] Date of Patent: Jul. 5, 1988

[54] APPARATUS FOR DETERMINING GRAIN SIZE

[75] Inventors: Marzio Giglio, Milan; Umberto Perrini, Lodi, both of Italy

[73] Assignee: Fritsch GmbH, Idar-Oberstein, Fed. Rep. of Germany

[21] Appl. No.: 871,068

[22] Filed: Jun. 5, 1986

[30] Foreign Application Priority Data

Jun. 7, 1985 [EP] European Pat. Off. ........ 85107037.5

[51] Int. Cl.$^4$ ............................................. G01N 21/53
[52] U.S. Cl. ...................................... 356/336; 356/343
[58] Field of Search ................. 250/573, 576; 356/335, 356/336, 343, 355

[56] References Cited

U.S. PATENT DOCUMENTS 3,830,569 8/1974 Meric .................................... 356/336
4,188,121 2/1980 Hirleman, Jr. et al. ............. 356/336

OTHER PUBLICATIONS

"Particle and Droplet Sizer", Powder Mettalugry International, vol. 10, No. 2, 5/1978, p. 99.
"Particle Size Analyzer", Applied Optics/vol. 11, No. 2, 2/1972, J. Cornillault, pp. 265-268.

Primary Examiner—Davis L. Willis
Assistant Examiner—Matthew W. Koren
Attorney, Agent, or Firm—Gifford, Groh, VanOphem, Sheridan, Sprinkle and Dolgorukov

[57] ABSTRACT

An apparatus for determining grain size distribution patterns of particles for selected measuring ranges, wherein a specimen cell (15) is arranged in a convergent monochromatic light beam (4) and the produced diffraction patterns (5a, 6a, 7a) are received by a photo detector. By altering the spacing of the specimen cell (15) from the photo detector (44), the measuring range can be selected for differing grain sizes.

10 Claims, 4 Drawing Sheets

APPARATUS FOR DETERMINING GRAIN SIZE

FIELD OF INVENTION

The invention relates to an apparatus for determining grain size distribution patterns of particles in suspensions and particularly for selected ranges of measurement wherein mineral particles can be found.

BACKGROUND OF INVENTION

When small particles are hit by light, refraction patterns of light result, depending on the size of the particles. This phenomena can be used in determining the size of the particles. In practice, monochromatic light is used in the form of a parallel beam which is allowed to strike a specimen cell in which the specimen or sample is located, and throws the diffraction patterns of the specimen onto a screen comprising a light sensitive detector means.

This has a number of annular light receiving elements, the radii of which are chosen according to the diffraction pattern expected so that the energy distribution of the diffraction pattern can be detected and delivered to an electronic analysing device which comprises a computer and calculates the grain size distribution of the respective specimen from the energy distribution detected.

Known apparatus found on the market for determining grain size have the disadvantage that on altering the measuring range, the image lens must be changed. However changing the image lens results in the whole system having to be adjusted, representing an extensive operation.

In a known process and apparatus for counting biological particles (Meric U.S. Pat. No. 3,830,569) two samples of blood cells are successively placed into the trajectory of the converging light beam at a distance D and D/1.8 respectively to obtain an analysis of blood particles. However, such system is not adapted to analyse grain size distribution patterns of mineral particles.

SUMMARY OF INVENTION

Therefore it is an object of the present invention to provide an apparatus for determining grain sizes of particle samples, the size distribution of which can be spread in a large range.

It is a further object of the present invention to provide an apparatus for determining grain size of mineral particle samples suspended in a fluid.

It is another object of the invention to make particle size measurements in a plurality of size ranges in a short time of say two minutes for every range.

Still another object is to provide an apparatus for determining grain size distribution of particles in a number of measuring ranges without having to change the lens of the optical system.

In accordance with the invention, the apparatus comprises a device for supplying suspended particles into a specimen cell, a laser for producing a monochromatic light beam, a photo detector means including a multiplicity of transducer elements, an optical system for concentrating the light beam onto said detector means and an analysis device for calculating grain size distributions based on the distribution pattern of light energy impinging on the transducer elements, and with regard to the selected measuring range, and wherein the optical system has an aperture and an image lens which reproduces the aperture on the photo detector means, a convergent beam being formed between the image lens, the specimen cell and the photo detector means, with the spacing of the specimen cell from the photo detector means being selected according to the range of measurement of interest.

With this apparatus a very large total measuring range of for example 1 to 1000 $\mu$m can be covered, where this large total measuring range is divided up into individual, selectable measuring ranges, in which the determining of grain size results according to 31 classes for example.

On altering the respectively selected measuring range no adjustment of the optical system is necessary. The measuring can be carried out automatically, as is somewhat necessary with process control. The measuring results obtained can be displayed on a video display unit which is attached to the computer. In the same way, a printer can be provided for indicating the results or magnetic tape for storing the results.

DESCRIPTION OF THE DRAWINGS

Further details of the invention are dealt with in the appending description and the accompanying drawings.

DESCRIPTION OF A PREFERRED EMBODIMENT

The apparatus for determining grain size contains three principle apparatus parts: a specimen conveying device 1, an optical measuring arrangement 2 and an analysis device 3.

Figure 4:
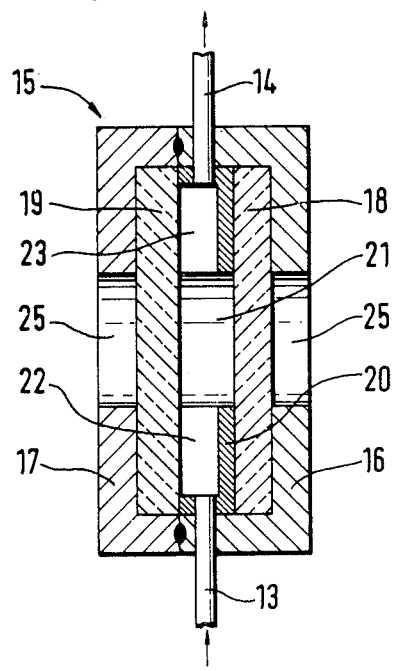
FIG. 4 shows a section through a specimen cell.
Figure 5:
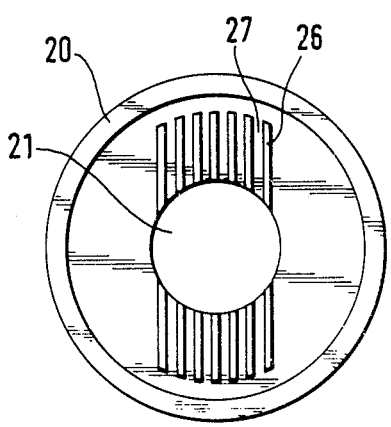
FIG. 5 shows a plan view of a detail of the specimen cell.

The specimen conveying device 1 contains a receptacle 10 for receiving the particles suspended in a suspension fluid, further a mixer 11 and a circulating pump 12, which is connected with a specimen cell 15 (FIG. 2) via a supply tube 13 and a return tube 14 (FIG. 1) and which is arranged within the optical measuring arrangement 2. Specimen cell 15 (FIG. 4) has an outer housing 16, 17 comprising two shells, and two plane parallel ground, light-permeable plates 18, 19 which are held spaced from one another by a spacer 20 and which enclose a measuring area 21 likewise stabilising areas 22 and 23. Housing shells 16, 17 and spacer 20 have respectively a central opening to form a window 25. Further the spacer 20 has ribs or guide walls 26 and arranged between these are slot-shaped channels 27, which extend parallel to one another between supply conduit 13 and outlet 14. These represent a means for producing a laminated flow for the fluid so that areas 22, 23, in which the guide walls 26 are arranged, can be described as stabilising areas for the fluid. If therefore suspension fluid together with the particles enters the measuring area 21, no or very little turbulence is produced and the danger of disintegration or of defective distribution of the particles in the suspension field is avoided.

Figure 1:
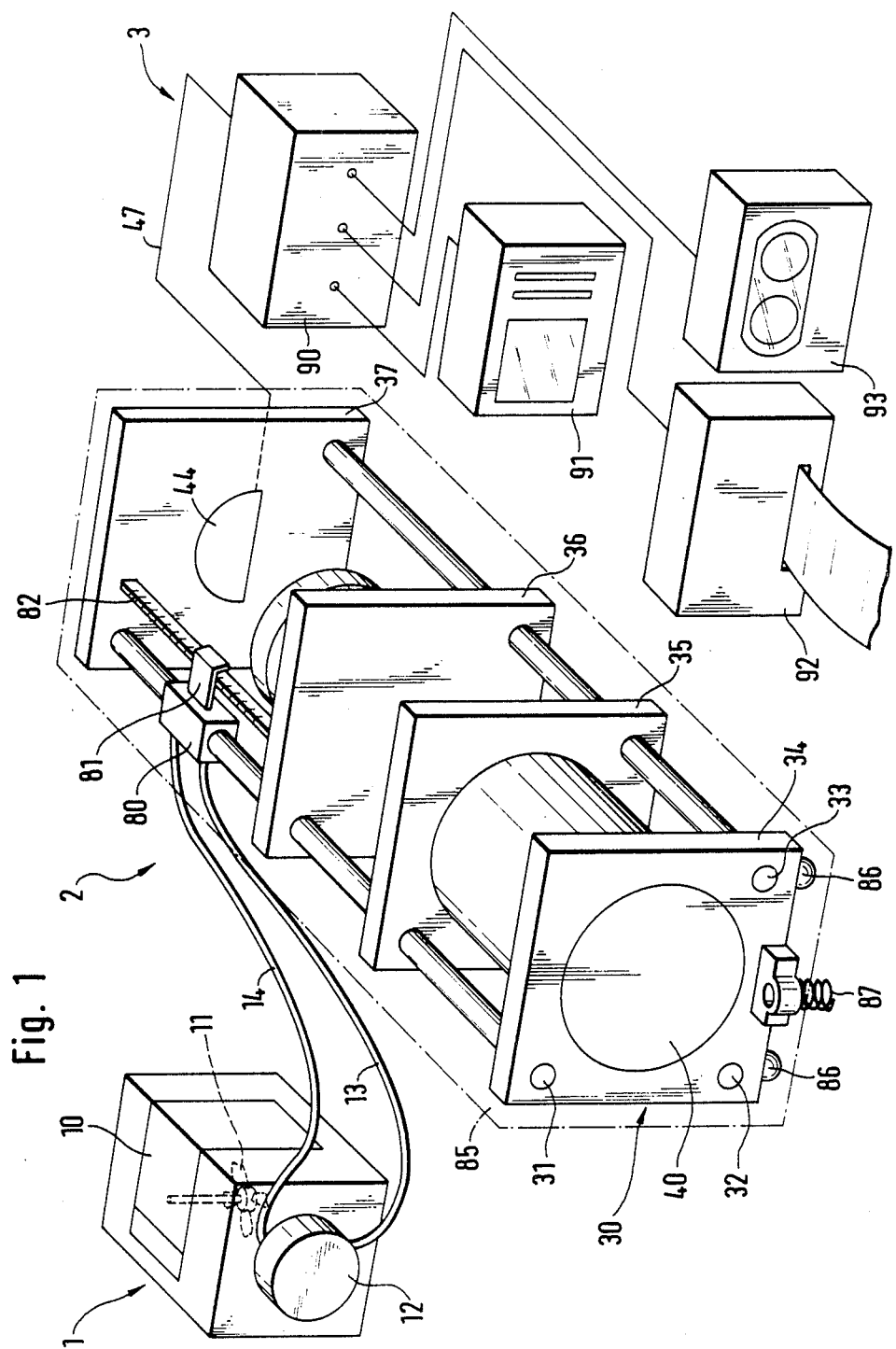
FIG. 1 is a schematic perspective view of the total apparatus.
Figure 2:
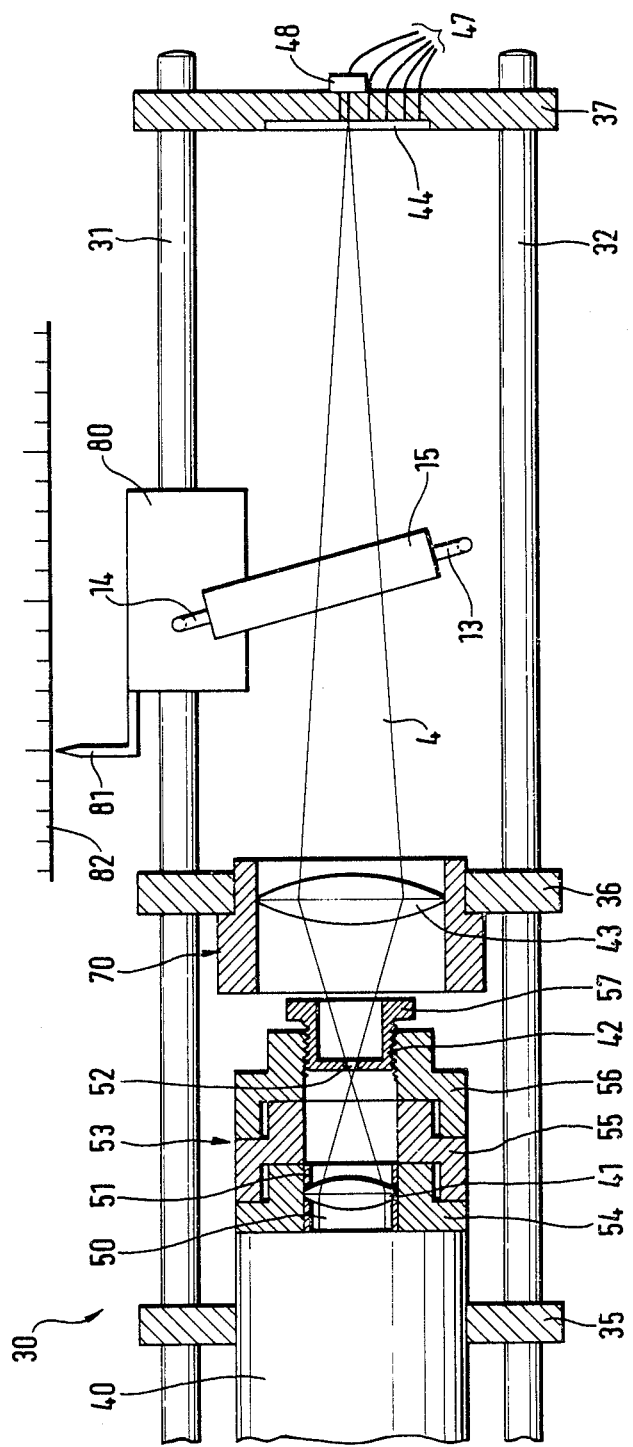
FIG. 2 shows a longitudinal section through a portion of the apparatus.
Figure 9:
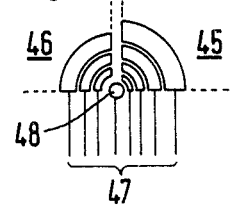
FIG. 9 is a schematic view on a portion of a detector means.

Optical measuring arrangement 2 encompasses a support or optical bench structure 30 which is shown in perspective in FIG. 1 yet schematically for the dimensions involved and in practice is about 1.20 m long. Bench structure 30 has three parallel rods 31, 32, 33, likewise four plates 34 to 37 which are secured to rods 31 to 33 for joining same. Plates 34 to 37 have respectively recesses for incorporating apparatus parts of the optical measuring arrangement, which remain in a rigid secure relation to one another due to the bench structure 30. In particular a laser 40 (FIG. 2) is secured in the recesses of plates 34, 35, a condenser lens 41 is fastened on laser 40, an aperture holder 42 is connected to the condenser lens 41, plate 36 supports an image lens 43, and a photo detector means 44 including thirty-one transducers is arranged on plate 37 with its thirty-one light receiving elements 45, 46 (FIG. 9) which are constructed as annular arcs and are arranged staggered in circular sectors. The intervals between the annular arcs 45 are covered by annular arcs 46, and likewise the intervals between annular arcs 46 are covered by annular arcs 45, if one thinks that the circular sectors being folded onto one another. The transducers provide electrical signals, so each of the annular arcs has two connecting electrodes which are connected with the analysis device 3 via conduits 47 (FIG. 1), likewise a photo detector 48 (FIG. 2) which is arranged in the center of curvature to the rings of the photo detector 44 and which is used on adjusting the apparatus.

Laser 40 (FIG. 2) emits a parallel beam 50 which should become focused on aperture 52 of aperture holder 42 by means of condenser lens 41. For this an initial adjustment of either condenser lens 41 or aperture holder 42 is necessary.

Figure 6:
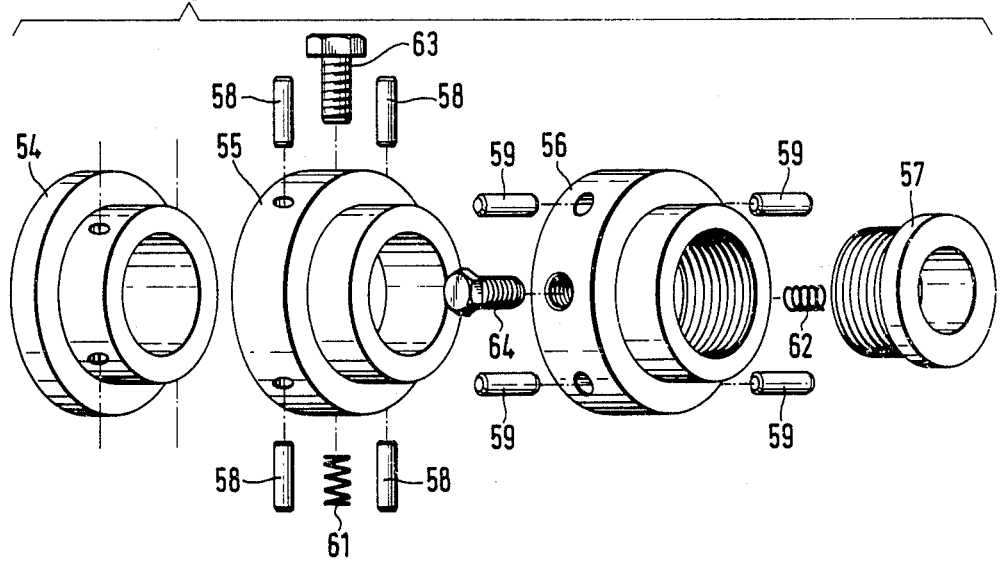
FIG. 6 is an exploded view on an aperture holder.

Usual lens securing means 51 are preferred for securing the condenser 41, and an adjustment device 53 for proper adjusting and securing in position of aperture holder 42 with respect to three axes X, Y and Z (see FIG. 6). For that purpose a stationary annular frame 54, an adjustment nut 57 and a pair of movable frames 55, 56 are provided, the latter are displaceable transversely to the optical axis. The aperture holder 42 is a part of the nut 57. The displacement of annular frames 55, 56 transversely to the optical axis is effected by means of a plurality of pins 58 and 59 which are arranged as guides in holes of the frames and extending in planes perpendicular to the optical axis. Frames 55, 56 are biased laterally by means of springs 61, 62 and can be moved thereagainst by means of adjustment screws 63 and 64. Thus an XY-adjustment transverse to the optical axis Z is possible with screws 63, 64 and a Z-adjustment in the direction of the optical axis is possible with adjustment nut 57.

Figure 7:
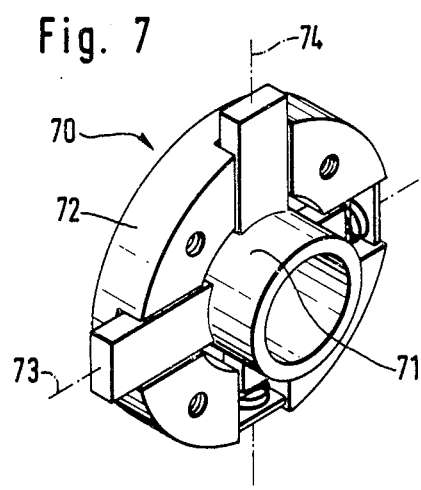
FIG. 7 is a perspective view on a lens holder.
Figure 8:
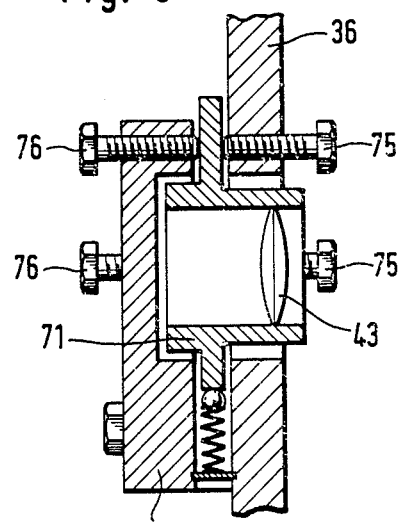
FIG. 8 is a sectional view of the lens holder.

The securing and adjustment of image lens 43 is by means of a lockable double Cardan mount 70 (see FIGS. 7 and 8). This contains two interfitting frames 71, 72 which are joined so as to allow frame 71 to pivot about crossed axes 73, 74, and the main plane of lens 43 can be aligned exactly perpendicular to the optical axis. Frame 71 is tilted by means of a pair of adjustment screws 75 until proper adjustment is reached and the proper adjustment can be secured by means of further screws 76.

Specimen cell 15 is connected with a bearing sleeve 80 (FIG. 2), which makes possible a rotation-free displacement along rod 31 as a guide. As is shown, the specimen cell 15 is arranged slightly inclined as compared with the optical axis, so that refelctions on the glasses 18, 19 are laterally deflected and do not appear disturbing during the measuring. Sleeve 80 enables the specimen cell 15 to be brought very close to the photo detector means 44—in this instance the measuring range is adjusted for the smallest grain size—or to move close to the image lens 43—in this case the large grain size range is detected—or an intermediate position is selected so as to measure intermediate grain size. Sleeve 80 has an indicator 81 which works together with a scale 82 and this makes it possible to read the exact position of specimen cell 15. This position is to be inputted into the analysis device 3. It is understood that this can also be made automatically by electrically scanning of the position of the sleeve 80.

In essence, the analysis device 3 encompasses a calculator or computer 90, attached to which is a video display unit or monitor 91. A data printer 92 or a magnetic recording apparatus 93 can also be attached to calculator or computer 90.

Figure 3:
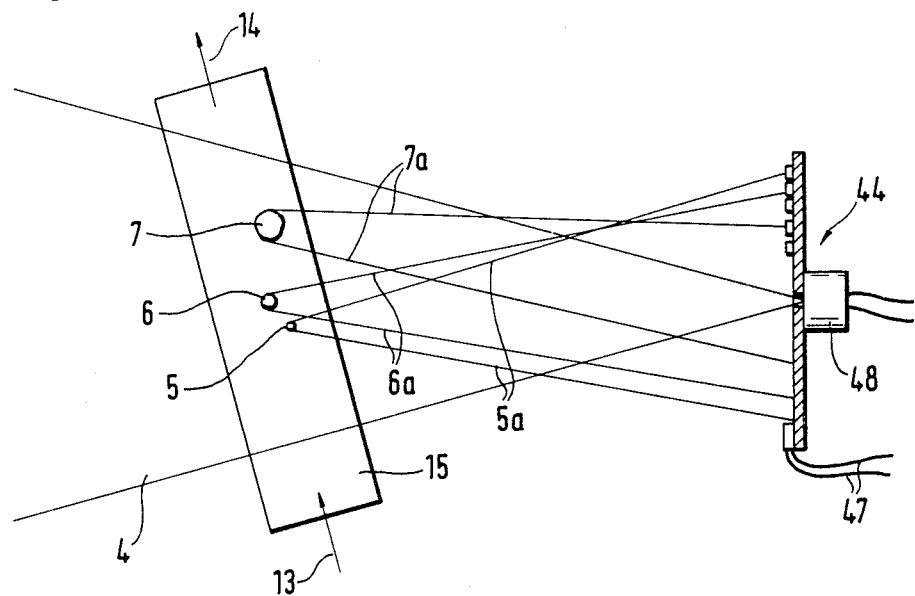
FIG. 3 shows an enlarged detail from FIG. 2.

The principle of measuring the grain size is shown in FIG. 3. Specimen cell 15 is arranged in a converging beam 4, the tip of which meets the central photo detector 48. In specimen cell 15, three particles 5, 6, 7 are beamed on, which produce correlated annular diffraction patterns, symbolised by corresponding cones 5a, 6a, 7a. The smallest particle 5 produces the widest cone of dispersion 5a, whilst the coarsest particle 7 produces the narrowest cone of dispersion 7a. The light impinging on photo detector means 44 is spread out over a wider area than the initial dot-shaped spot by means of the presence of particles in the specimen cell, and the intensity distribution is detected sufficiently fine due to the 31 light receiving elements 45, 46.

The evaluation of this light distribution in computer 90 can result in differing ways. For example it is possible to assume a specific grain size distribution, to calculate a light distribution from same on the screen 44, 48 and to compare this with the actually measured light distribution. The deviations are used for correcting the model of the grain size distribution until the approximation is sufficiently fine, and then such approximation is used as the obtained grain size distribution.

So as to avoid thermal and mechanical disturbing influences on the adjusted optical system, the bench structure 30 is supported to "float" in the outer housing 85 (FIG. 1). To this end there are ball bearings 86 and two or more spring loaded pin connections 87 allowing a shifting movement for example of plates 35 and 37 to the outer housing 85 along crossed axes.

Instead of using suspended particles in a suspension liquid it is also possible to analyse a "dry" particle stream or jet which for example is included in a directed air stream. Droplets can also be measured as "particles" in respect to their size in an air or gas flow.

The number of the transducers determines the number of classes, wherein the particle size is to be classified. Therefore, more than thirty-one transducers could be used. If the number of transducers is below nine, the size determination will become too coarse.

What is claimed is:

1. An apparatus for determining grain size distribution patterns of particles for selected ranges of measurement comprising:
   a laser for producing a monochromatic light beam;
   a detector means including a plurality of at least nine transducer elements for delivering electrical signals representing distribution patterns of impinging light energy;

an optical system for directing said light beam onto said detector means and defining an optical axis, said optical system including an aperture and a lens focussing said light beam from said aperture onto said detector means so as to produce a convergent light beam impinging said detector means;

an analyzing device for calculating grain size distribution patterns based on said light energy distribution pattern signals and with regard to said selected range of measurement;

a device for supplying said particles into a specimen cell; and a holder means for said specimen cell having bearing means and displaceable along and lockable in a stationary guideway extending parallel to said optical axis, whereby said specimen cell is spaced apart a predetermined spacing from said detector means in said converging beam to determine said selected range of measurement.

2. An apparatus according to claim 1 wherein said holder means has an indicator means cooperating with a stationary scale to indicate said spacing between said specimen cell and said detector means.

3. An apparatus according to claim 1 wherein said device for supplying said particles to said specimen cell is a fluid pumping device and wherein said specimen cell comprises two plane parallel ground, light-permeable plates which enclose a measuring area and at least one stabilising area, the latter including means for producing a laminar flow of said fluid supplied by said pumping device.

4. An apparatus according to claim 3 wherein said means for producing said laminar flow comprises parallel guide wall means and slot-shaped channel means arranged between said wall means.

5. An apparatus according to claim 1 wherein said at least nine transducer elements comprise a number of between nine (9) and forty-one (41) surface elements shaped like annular arcs and being arranged in circular sectors, said annular arcs being staggered relative to each other in sectors.

6. An apparatus according to claim 1 further comprises an outer housing, a bench structure and means for floatably supporting said bench structure within said outer housing, said outer housing and said bench structure adapted for receiving said laser, said optical system, said specimen cell, and said detector means, said bench structure having rod means arranged parallel to one another and plate means secured between said rod means.

7. An apparatus according to claim 6 wherein said plate means have recesses arranged along the length of said optical axis, said laser and said optical system being retained by securing means within said recesses of said plate means.

8. An apparatus according to claim 1 wherein said aperture of said optical system comprises two frame members including bearing means and locking means displaceable and lockable transversely to said optical axis and a nut which is adjustable in the direction of said optical axis.

9. An apparatus according to claim 1 wherein said optical system comprises a lens holder including a stationary member and a tiltable member and means for adjusting and locking said tiltable member with respect to said stationary member.

10. An apparatus according to claim 1 wherein said pluraltiy of said transducer elements comprises thirty-one surface elements arranged as annular arcs with said optical axis being the center of curvature, said surface elements forming two rows which are staggered with respect to one another.

* * * * *